(12) United States Patent
Kuwahara et al.

(10) Patent No.: US 10,233,423 B2
(45) Date of Patent: Mar. 19, 2019

(54) METHOD FOR MANUFACTURING CILIARY MARGINAL ZONE-LIKE STRUCTURE

(71) Applicants: SUMITOMO CHEMICAL COMPANY, LIMITED, Tokyo (JP); RIKEN, Wako-shi, Saitama (JP)

(72) Inventors: Atsushi Kuwahara, Osaka (JP); Yoshiki Sasai, Kobe (JP)

(73) Assignees: SUMITOMO CHEMICAL COMPANY, LIMITED, Tokyo (JP); RIKEN, Wako (JP)

( * ) Notice: Subject to any disclaimer, the term of this patent is extended or adjusted under 35 U.S.C. 154(b) by 0 days.

(21) Appl. No.: 15/103,162

(22) PCT Filed: Oct. 16, 2014

(86) PCT No.: PCT/JP2014/077602
§ 371 (c)(1),
(2) Date: Jun. 9, 2016

(87) PCT Pub. No.: WO2015/087614
PCT Pub. Date: Jun. 18, 2015

(65) Prior Publication Data
US 2016/0376554 A1 Dec. 29, 2016

(30) Foreign Application Priority Data
Dec. 11, 2013 (JP) .................................. 2013-255836

(51) Int. Cl.
*C12N 5/079* (2010.01)
*A61L 27/36* (2006.01)
*A61K 35/30* (2015.01)
*A61K 9/00* (2006.01)
*G01N 33/50* (2006.01)
*A61L 27/38* (2006.01)

(52) U.S. Cl.
CPC .......... *C12N 5/0621* (2013.01); *A61K 9/0051* (2013.01); *A61K 35/30* (2013.01); *A61L 27/3641* (2013.01); *A61L 27/3687* (2013.01); *A61L 27/3804* (2013.01); *G01N 33/5008* (2013.01); *G01N 33/5014* (2013.01); *A61L 2300/64* (2013.01); *A61L 2430/16* (2013.01); *C12N 2500/90* (2013.01); *C12N 2501/119* (2013.01); *C12N 2501/155* (2013.01); *C12N 2501/385* (2013.01); *C12N 2501/415* (2013.01); *C12N 2501/727* (2013.01); *C12N 2501/73* (2013.01); *C12N 2506/02* (2013.01); *C12N 2506/45* (2013.01); *C12N 2513/00* (2013.01)

(58) Field of Classification Search
CPC ............ C12N 5/0621; C12N 2501/727; C12N 2513/00; C12N 2501/155; C12N 2506/02; C12N 2501/385; C12N 2501/415; C12N 2506/45; C12N 2501/73; C12N 2501/119; C12N 2500/90; A61L 27/3687; A61L 27/3641; A61L 27/3804; A61L 2300/64; A61L 2430/16; A61K 9/0051; A61K 35/30; G01N 33/5008; G01N 33/5014
See application file for complete search history.

(56) References Cited

U.S. PATENT DOCUMENTS
2015/0132787 A1 5/2015 Sasai et al.

FOREIGN PATENT DOCUMENTS
WO WO 2013/183774 A1 12/2013

OTHER PUBLICATIONS

Komiya et al. Wnt signal transduction pathways. Organogenesis 4:2, 68-75; Apr./May/Jun. 2008 (Year: 2008).*
Kubo et al. Wnt2b controls retinal cell differentiation at the ciliary marginal zone. Development 130, 587-598 (Year: 2003).*
Bhatia et al., "Distribution of Müller stem cells within the neural retina: Evidence for the existence of ciliary margin-like zone in the adult human eye," *Experimental Eye Research*, 89(3): 373-382 (2009).
Fuhrmann, "Wnt signaling in eye organogenesis," *Organogenesis*, 4(2): 60-67 (2008).
Inoue et al., "Activation of Canonical Wnt Pathway Promotes Proliferation of Retinal Stem Cells Derived from Adult Mouse Ciliary Margin," *Stem Cells*, 24(1): 95-104 (2006).
Kubo et al., "Hairy1 acts as a node downstream of Wnt signaling to maintain retinal stem cell-like progenitor cells in the chick ciliary marginal zone," *Development*, 136(11): 1823-1833 (2009).

(Continued)

*Primary Examiner* — Taeyoon Kim
(74) *Attorney, Agent, or Firm* — Leydig, Voit & Mayer, Ltd.

(57) ABSTRACT

The present invention provides a method for producing a cell aggregate containing a ciliary marginal zone-like structure, including a step of culturing a cell aggregate containing a retinal tissue in which Chx10 positive cells are present in a proportion of 20% or more and 100% or less of the tissue in a serum-free medium or serum-containing medium each containing a substance acting on the Wnt signal pathway and a substance inhibiting the FGF signal pathway for only a period before the appearance of a RPE65 gene expressing cell, followed by culturing the "cell aggregate in which a RPE65 gene-expressing cell does not appear" thus obtained in a serum-free medium or serum-containing medium each free of a substance acting on the Wnt signal pathway and so on. According to the production method of the present invention, a ciliary marginal zone-like structure can be produced with high efficiency.

20 Claims, 4 Drawing Sheets

(56) References Cited

OTHER PUBLICATIONS

Nakano et al., "Self-Formation of Optic Cups and Storable Stratified Neural Retina from Human ESCs," *Cell Stem Cell*, 10(6): 771-785 (2012).
Stephens et al., "Loss of *Adenomatous polyposis coli* (apc) Results in an Expanded Ciliary Marginal Zone in the Zebrafish Eye," *Developmental Dynamics*, 239(7): 2066-2077 (2010).
Japanese Patent Office, International Preliminary Report on Patentability in International Patent Application No. PCT/JP2013/065878 (dated Dec. 9, 2014).
Japanese Patent Office, International Search Report in International Patent Application No. PCT/JP2013/065878 (dated Jul. 30, 2013).
Bhatia et al., "Adult Retinal Stem Cells Revisited," *Open Ophthamol. J.*, 4: 30-38 (2010).
Eiraku et al., "Self-organizing optic-cup morphogenesis in three-dimensional culture," *Nature*, 472(7341): 51-56 (2011).
Fischer et al., "The ciliary marginal zone (CMZ) in development and regeneration of the vertebrate eye," *Exp. Eye Res.*, 116: 199-204 (2013).
Hedge et al., "Expression of Shisa2, a modulator of both Wnt and Fgf signaling, in the chick embryo," *Int. J. Dev. Biol.*, 52(1): 81-85 (2008).
Kuwahara et al., "Generation of a ciliary margin-like stem cell niche from self-organizing human retinal tissue," *Nat. Commun.*, 6: 6286 (2015).
Liu et al., "Ciliary margin transdifferentiation from neural retina is controlled by canonical Wnt signaling," *Dev. Biol.*, 308(1): 54-67 (2007).
Moshiri et al., "Sonic Hedgehog Regulates Proliferation of the Retinal Ciliary Marginal Zone in Posthatch Chicks," *Dev. Dyn.*, 233(1): 66-75 (2005).
Spence et al., "The hedgehog pathway is a modulator of retina regeneration," *Development*, 131(18): 4607-4621 (2004).
European Patent Office, Extended European Search Report in European Patent Application No. 14869571.1 (dated Jun. 7, 2017).
Intellectual Property Office of Singapore, Search Report in Singaporean Patent Application No. 11201604705U (dated May 5, 2017).
Phillips et al., "Blood-Derived Human iPS Cells Generate Optic Vesicle-Like Structures with the Capacity to Form Retinal Laminae and Develop Synapses," *Invest. Ophthalmol. Vis. Sci.*, 53(4): 2007-2019 (2012).

* cited by examiner

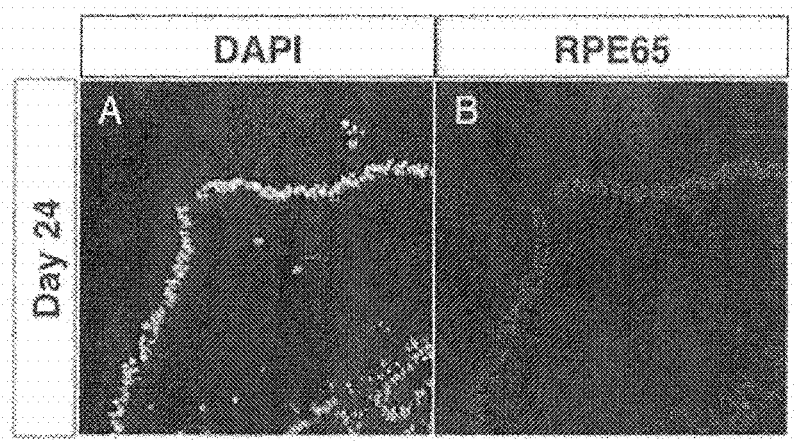

METHOD FOR MANUFACTURING CILIARY MARGINAL ZONE-LIKE STRUCTURE

CROSS-REFERENCE TO RELATED APPLICATIONS

This patent application is the U.S. national phase of International Patent Application No. PCT/JP2014/077602, filed Oct. 16, 2014, which claims the benefit of Japanese Patent Application No. 2013-255836, filed on Dec. 11, 2013, which are incorporated by reference in their entireties herein.

TECHNICAL FIELD

The present invention relates to a method for producing a ciliary marginal zone-like structure, and so on.

BACKGROUND ART

The ciliary marginal zone (CMZ) of the in vivo retina is known to perform important functions for the structural formation and maintenance of retinal tissues (see, for example, non-patent document 1) and, for example, Rdh10 gene (non-patent document 2) and Otx1 gene (non-patent document 1) are known as gene markers of the ciliary marginal zone.

DOCUMENT LIST

Non-Patent Documents non-patent document 1: DEVELOPMENTAL DYNAMICS, Volume:239, Pages:2066-2077 (2010)
non-patent document 2: Development, Volume:136, Pages: 1823-1833 (2009)

SUMMARY OF THE INVENTION

Problems to be Solved by the Invention

There has been a desire to develop a method for producing a ciliary marginal zone-like structure with high efficiency.

Means of Solving the Problems

The present invention provides a method for producing a ciliary marginal zone-like structure from a cell aggregate comprising a retinal tissue, and so on.
Specifically, the present invention provides:
1. a method for producing a cell aggregate comprising a ciliary marginal zone-like structure, comprising a step of culturing a cell aggregate comprising a retinal tissue in which Chx10 positive cells are present in a proportion of 20% or more and 100% or less of the tissue in a serum-free medium or serum-containing medium each containing a substance acting on the Wnt signal pathway and a substance inhibiting the FGF signal pathway for only a period before the appearance of a RPE65 gene-expressing cell, followed by culturing the resulting "cell aggregate in which a RPE65 gene-expressing cell does not appear" in a serum-free medium or serum-containing medium each free of a substance acting on the Wnt signal pathway (hereinafter, sometimes referred to as the production method of the present invention);
2. the production method of the above-mentioned 1, wherein the cell aggregate in which a RPE65 gene-expressing cell does not appear is a cell aggregate in which Chx10 positive cells are present in the retinal tissue in a proportion of within 30% to 0% of the tissue;
3. the production method of the above-mentioned 1 or 2, wherein the resulting "cell aggregate in which a RPE65 gene-expressing cell does not appear" is cultured in a serum-free medium or serum-containing medium each free of a substance acting on the Wnt signal pathway until the proportion of Chx10 positive cells present in the retinal tissue reaches 30% or more of the tissue;
4. the production method of any one of the above-mentioned 1 to 3, wherein the retinal tissue is derived from a human pluripotent stem cell;
5. use of a cell aggregate comprising a ciliary marginal zone-like structure produced by the production method of any one of the above-mentioned 1 to 4, as a reagent for evaluating toxicity or drug efficacy;
6. a method for evaluating toxicity or drug efficacy of a test substance, comprising contacting the substance with a cell aggregate comprising a ciliary marginal zone-like structure produced by the production method of any one of the above-mentioned 1 to 4, and assaying an influence of the substance on the structure or the aggregate;
7. use of a cell aggregate comprising a ciliary marginal zone-like structure produced by the production method of any one of the above-mentioned 1 to 4, as a biological material for transplantation;
8. a method of treating a disease due to a disorder of retinal tissue, comprising transplanting an effective amount of cell aggregate comprising a ciliary marginal zone-like structure produced by the production method of any one of the above-mentioned 1 to 4 to a subject in need of the transplantation;
9. a cell aggregate comprising a ciliary marginal zone-like structure produced by the production method of any one of the above-mentioned 1 to 4, which is for use for the treatment of a disease due to a disorder of the ciliary marginal zone-like structure; and so on.

Effect of the Invention

According to the production method of the present invention, a ciliary marginal zone-like structure can be produced with high efficiency. In a cell aggregate comprising a ciliary marginal zone-like structure produced by the production method of the present invention, the ciliary marginal zone-like structure functions as a progress zone, and there can be formed with high frequency a continuous neural retina having a layer structure adjacent to the ciliary marginal zone-like structure.

show immunostained images of Chx10 positive cells, and "B" and "D" show immunostained images of MITF positive cells.

Figure 3:
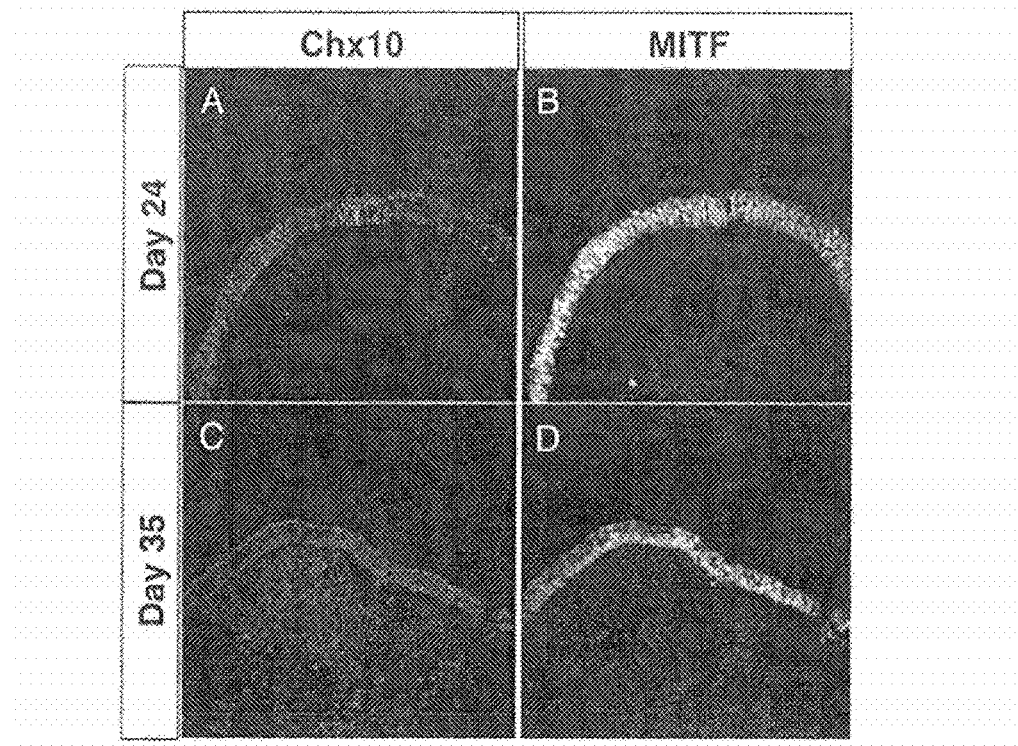

FIG. 3 shows stained images of a cryosection of cell aggregates obtained by floating culture of cell aggregates containing a retinal tissue (on day 18 from the start of the floating culture) in a serum-free medium containing a substance acting on the Wnt signal pathway and a substance inhibiting FGF signal pathway for 6 days, i.e., up to day 24 from the start of the floating culture (A,B), and a cell aggregate obtained by further floating culture of the aforementioned cell aggregate (on day 24 from the start of the floating culture) in a serum-containing medium containing a substance acting on the Wnt signal pathway and free of a substance inhibiting FGF signal pathway for 11 days, i.e., up to day 35 from the start of the floating culture (C,D). "A" and "C" are immunostained images of Chx10 positive cells, and "B" and "D" are immunostained images of MITF positive cells.

Figure 4:
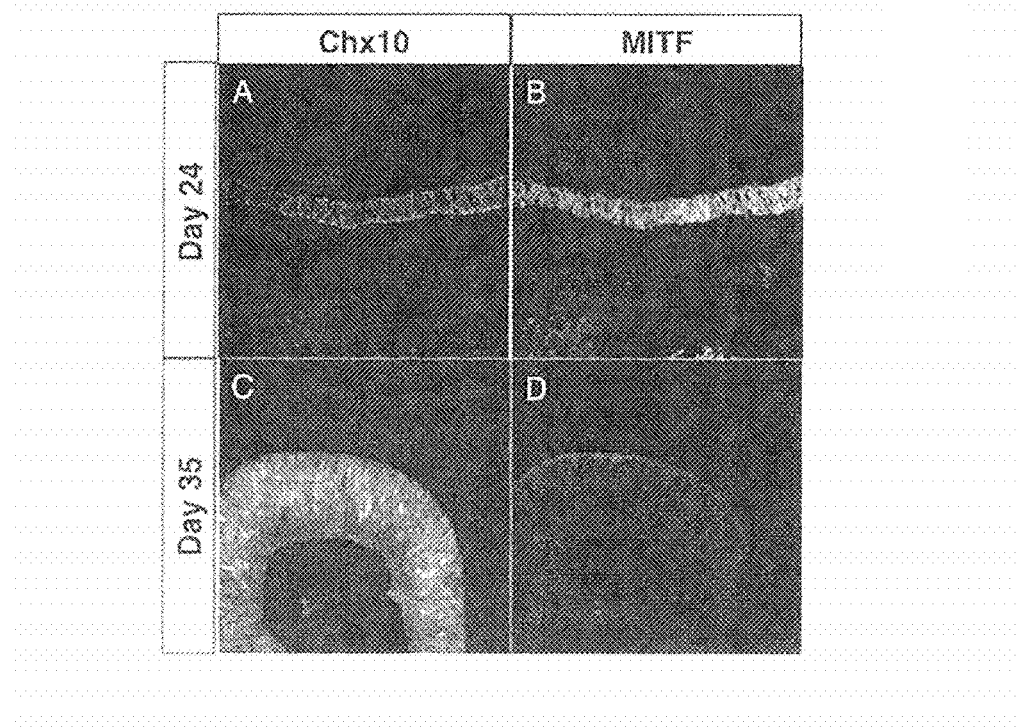

FIG. 4 shows stained images of a cryosection of cell aggregates obtained by floating culture of cell aggregates containing a retinal tissue (on day 18 from the start of the floating culture) in a serum-free medium containing a substance acting on the Wnt signal pathway and a substance inhibiting FGF signal pathway for 6 days, i.e., up to day 24 from the start of the floating culture (A,B), and a cell aggregate obtained by further floating culture of the aforementioned cell aggregate (on day 24 from the start of the floating culture) in a serum-containing medium free of a substance acting on the Wnt signal pathway and a substance inhibiting FGF signal pathway for 11 days, i.e., up to day 35 from the start of the floating culture (C,D). "A" and "C" are immunostained images of Chx10 positive cells, and "B" and "D" are immunostained images of MITF positive cells.

Figure 5:
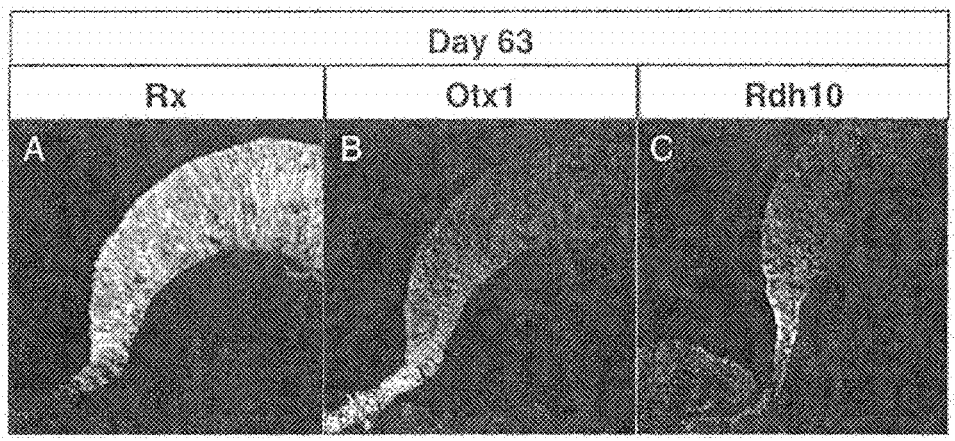

FIG. 5 shows stained images of a cryosection of cell aggregates obtained by floating culture of cell aggregates containing a retinal tissue (on day 18 from the start of the floating culture) in a serum-free medium containing a substance acting on the Wnt signal pathway and a substance inhibiting FGF signal pathway for 6 days, and further floating culture in a serum containing medium free of a substance acting on the Wnt signal pathway and a substance inhibiting FGF signal pathway for 39 days, i.e., up to day 63 from the start of the floating culture. "A" (Rx) is a GFP fluorescence image of Rax gene-expressing cell, "B" is an immunostained image of Otx1 positive cell, and "C" is an immunostained image of Rdh10 positive cell.

Figure 6:
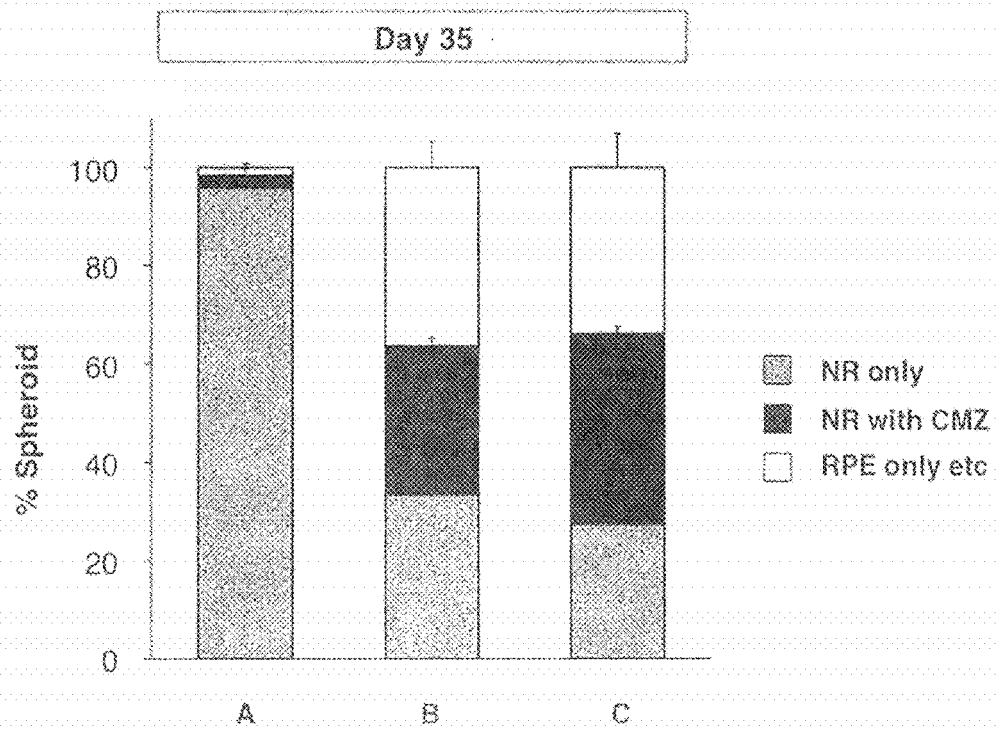

FIG. 6 is a graph showing the proportion of a cell aggregate containing neural retina alone (gray bar graph), proportion of a cell aggregate containing neural retina formed continuously from the ciliary marginal zone-like structure (black bar graph), and proportion of a cell aggregate free of neural retina and containing retinal pigment epithelium and other tissues (white bar graph), in cell aggregates on day 35 from the start of the floating culture, which were obtained by floating culture of cell aggregates containing a retinal tissue (on day 18 from the start of the floating culture) under the three conditions (A,B,C) described in Example 4.

FIG. 7 shows stained images of a cryosection of cell aggregates obtained by floating culture of cell aggregates containing a retinal tissue (on day 18 from the start of the floating culture) in a serum-free medium containing a substance acting on the Wnt signal pathway and a substance inhibiting FGF signal pathway for 6 days, i.e., up to day 24 from the start of the floating culture (A,B). "A" is a DAPI stained image of the cell nucleus, and "B" is an immunostained image of RPE65 positive cell.

DESCRIPTION OF EMBODIMENTS

The mode for carrying out the present invention is explained in detail below.

In the present invention, examples of the "stem cell" include a cell that maintains the same differentiation capacity even after cell division and can regenerate a tissue when it is injured. Here, the "stem cell" may be an embryonic stem cell (ES cell) or a tissue stem cell (also called tissular stem cell, tissue-specific stem cell or somatic stem cell), or an artificial pluripotent stem cell (iPS cell: induced pluripotent stem cell) but is not limited thereto. As is appreciated from the fact that the stem cell-derived tissue cell can regenerate a tissue, it is known that the stem cell can differentiate into a normal cell close to one in a living body.

Examples of the "pluripotent stem cell" in the present invention include a stem cell that can be cultured in vitro and has an ability to differentiate into any cell (triploblast (ectoderm, mesoderm, endoderm)-derived tissue) constituting a living body except for placenta (pluripotency), including an embryonic stem cell (ES cell). The "pluripotent stem cell" is obtained from fertilized egg, clone embryo, reproductive stem cell, and stem cell in a tissue. It also includes a cell having induced pluripotent similar to that of embryonic stem cells, after introducing several kinds of genes into a somatic cell (also called artificial pluripotent stem cell). Pluripotent stem cell can be produced by a method known per se. Examples of the production method of the pluripotent stem cell include the methods described in Cell 131(5) pp. 861-872 (2007), Cell 126(4) pp. 663-676 (2006), etc.

Examples of the "embryonic stem cell (ES cell)" in the present invention include a stem cell having a self replication ability and multipotency (particularly, "pluripotency"), which is a pluripotent stem cell derived from an early embryo. Embryonic stem cell was first established in 1981, and has also been applied to the generation of knockout mouse since 1989. In 1998, a human embryonic stem cell was established, which is also being utilized for regenerative medicine.

Examples of the "artificial pluripotent stem cell" in the present invention include a cell induced to have pluripotency by directly reprogramming a differentiated cell such as fibroblast etc. by the expression of several kinds of genes such as Oct3/4, Sox2, Klf4, and Myc, which was established by Yamanaka's group. in mouse cell in 2006 (Takahashi K and Yamanaka S. Cell. 2006, 126(4), p 663-676). In 2007, the artificial pluripotent stem cell was also established in human fibroblast, and has pluripotency similar to that of embryonic stem cells (Cell, 2007, 131(5), p861-872; Science, 2007, 318(5858), p1917-1920; Nat Biotechnol., 2008, 26(1), p101-106).

Pluripotent stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from Incorporated Administrative Agency RIKEN, and D3 cell line is available from ATCC, respectively.

Pluripotent stem cell can be maintained by culturing according to a method known per se. For example, human stem cell can be maintained by culturing using Knockout™ Serum Replacement (KSR). For example, mouse stem cell can be maintained by culturing with addition of fetal bovine serum (FBS) and a leukemia inhibitory factor (LIF), and without feeder cell.

Examples of the "aggregate" in the present invention include a mass of the cells dispersed in the medium but gathered to form same. The "aggregate" in the present invention includes an aggregate formed by the cells dispersed at the start of the floating culture and an aggregate already formed at the start of the floating culture.

When cells gather to form cell aggregates and the aggregates are subjected to floating culture, to "form aggregate" means to "rapidly aggregate a given number of dispersed stem cells" to form qualitatively uniform cell aggregates. For example, when pluripotent stem cells are rapidly gathered to allow for formation of an aggregate of the pluripotent stem cells, an epithelium-like structure can be formed with good reproducibility in the cells induced to differentiate from the formed aggregate.

Examples of the experimental operation to form an aggregate include a method involving keeping cells in a small space by using a plate with small wells (96 well plate), micropore and so on, a method involving aggregating cells by centrifugation for a short time using a small centrifugation tube, and so on.

Examples of the "tissue" in the present invention include a structure of a cell population, which has a conformation wherein more than one type of cell different in the shape and property are sterically configured in a given pattern.

In the present invention, examples of the "retinal tissue" include a retinal tissue etc. wherein at least two or more types of cells such as photoreceptors, horizontal cells, bipolar cells, amacrin cells, retinal ganglion cells, their progenitor cells, retinal progenitor cells thereof and so on, which constitute respective retinal layers in in vivo retina, are sterically arranged in layers. With regard to each cell, which cell constitutes which retinal layer can be confirmed by a known method, for example, presence or absence of the expression of a cell marker or the level thereof, etc.

As the "retinal tissue" in the present invention, an epithelial tissue containing a retinal progenitor cell or neural retinal progenitor, which can be formed on a surface of a cell aggregate of pluripotent stem cells by floating culture of the aggregate under conditions suitable for differentiation into retina, can also be mentioned.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

As the "retinal progenitor cell" in the present invention, a progenitor cell capable of differentiating into any mature retina cell constituting the neural retina and the retinal pigment epithelium can be mentioned.

As the "neural retinal progenitor", a progenitor cell which is a cell destined to form an inner layer of the optic cup and capable of differentiating into any mature cell constituting the neural retina can be mentioned.

Examples of the retinal cell marker include Rax and PAX6 expressed in retinal progenitor cell, Chx10 expressed in neural retinal progenitor cell, Nkx2.1 expressed in progenitor cell of hypothalamus neuron but not expressed in retinal progenitor cell, Sox1 expressed in hypothalamus neuroepithelium but not expressed in retina, Crx expressed in progenitor cell of photoreceptor cell, and so on. Examples of the marker of the retinal layer-specific neuron include Chx10 and L7 expressed in bipolar cell, TUJI and Brn3 expressed in ganglion cell, Calretinin expressed in amacrine cell, Calbindin expressed in horizontal cell, Rhodopsin and Recoverin expressed in photoreceptor cell, RPE65 and Mitf expressed in pigment epithelium cell, Nrl expressed in rod cell, Rxr-gamma expressed in cone cell and so on.

Examples of the "ciliary marginal zone (CMZ)" in the present invention include a tissue present in the boundary region of retinal tissue (specifically, neural retina) and retinal pigment epithelium in the in vivo retina, which is a region including a tissue stem cell of retina (retinal stem cell). Ciliary marginal zone is also called a ciliary margin or retinal margin, and the ciliary marginal zone, ciliary margin and retinal margin are equivalent tissues. It is known that the ciliary marginal zone plays an important role in the supply of retinal progenitor cells and differentiated cells to retinal tissues, maintenance of retinal tissue structure and so on. Examples of the marker gene of the ciliary marginal zone include Rdh10 gene (positive), Otx1 gene (positive) and so on.

Examples of the "progress zone" in the present invention include a population of undifferentiated cells localized in a part of a tissue, and examples thereof include a population of cells having properties to continuously grow in the process of development and regeneration to contribute to the growth of a tissue as a whole and/or properties to contribute to the growth of the surrounding tissues by secreting a growth factor etc. Specific examples of the progress zone include a population of undifferentiated cells at the tip of a limb bud.

The "medium" to be used in the present invention can be prepared from a medium used for culture of animal cell as a basal medium. Examples of the basal medium include media that can be used for culturing animal cells such as BME medium, BGJb medium, CMRL1066 medium, Glasgow MEM medium, Improved MEM Zinc Option medium, IMDM medium, Medium199 medium, Eagle MEM medium, αMEM medium, DMEM medium, ham medium, F-12 medium, DMEM/F-12 medium, RPMI1640 medium, Fischer's medium, and mixed medium thereof etc.

Examples of the "serum-free medium" in the present invention include a medium free of unadjusted or unpurified serum. In the present invention, a medium containing purified blood-derived components and animal tissue-derived components (e.g., growth factor) is also included in a serum-free medium unless unadjusted or unpurified serum is contained therein.

The serum-free medium may contain a serum replacement. Examples of the serum replacement include albumin, transferrin, fatty acid, collagen precursor, trace element, 2-mercaptoethanol or 3' thiolglycerol, one appropriately containing equivalents of these etc., and so on. Such serum replacement may be prepared by, for example, the method described in WO98/30679 and so on. In addition, the serum replacement may be a commercially available product. Examples of such commercially available serum replacement include Knockout™ Serum Replacement (Invitrogen: hereinafter sometimes to be indicated as KSR), Chemically Defined Lipid Concentrate (manufactured by Gibco) and Glutamax (manufactured by Gibco).

The "serum-free medium" to be used for floating culture may contain fatty acid, lipid, amino acid (e.g., non-essential amino acid), vitamin, growth factor, cytokine, antioxidant, 2-mercaptoethanol, pyruvic acid, buffering agent, inorganic salts and so on.

To avoid complicated preparation, a serum-free medium (GMEM or DMEM medium, supplemented with 0.1 mM 2-mercaptoethanol, 0.1 mM non-essential amino acid Mix and 1 mM sodium pyruvate; or a 1:1 mixture of F-12 medium and IMDM medium supplemented with 450 μM 1-monothioglycerol etc.) supplemented with an appropriate amount (e.g., about 1-about 20%) of commercially available KSR can be preferably mentioned as the serum-free medium.

Examples of the "serum-containing medium" in the present invention include a medium containing unadjusted or unpurified serum. The medium may contain fatty acid, lipid, amino acid (e.g., non-essential amino acid), vitamin, growth factor, cytokine, antioxidant, 2-mercaptoethanol, pyruvic acid, buffering agent, inorganic salts and so on.

Examples of the "serum" to be added to the medium in the present invention include mammalian sera such as bovine serum, calf serum, fetal bovine serum, horse serum, colt serum, fetal horse serum, rabbit serum, leveret serum, fetal rabbit serum, and human serum, and so on.

In the present invention, the "medium containing substance X" is a medium supplemented with an exogenous substance X or a medium containing an exogeneous substance X, and the "medium free of substance X" is a medium not supplemented with an exogenous substance X or a medium free of an exogeneous substance X. As used herein, the "exogeneous substance X" means substance X exogeneous to the cell or tissue cultured in the medium, and excludes endogenous substance X produced by the cell or tissue.

For example, the "medium containing a substance acting on the Wnt signal pathway" is a medium supplemented with an exogeneous substance acting on the Wnt signal pathway or a medium free of an exogeneous substance acting on the Wnt signal pathway. The "medium free of a substance inhibiting FGF signal pathway" is a medium not supplemented with an exogeneous substance inhibiting FGF signal pathway or a medium free of an exogeneous substance inhibiting FGF signal pathway.

Examples of the "floating culture" in the present invention include culture of cell aggregates in a medium under nonadhesive conditions to a cell culture vessel, and so on.

The cell culture vessel to be used in floating culture is not particularly limited as long as it enables floating culture of the cells. Examples of such cell culture vessel include flask, tissue culture flask, dish, petri dish, tissue culture dish, multidish, microplate, microwell plate, micropore, multiplate, multiwell plate, chamber slide, schale, tube, tray, culture bag, roller bottle and so on. A preferable vessel is a cell non-adhesive vessel.

As a cell non-adhesive vessel, one having its surface not artificially treated to improve cell adhesiveness (e.g., coating treatment with extracellular matrix, etc.) and so on may be used. As a cell non-adhesive vessel, a vessel having a surface artificially treated to lower adhesiveness to the cells (e.g., superhydrophobic treatment) etc. may be used.

The production method of the present invention characteristically includes a step of culturing a cell aggregate comprising a retinal tissue in which Chx10 positive cells are present in a proportion of 20% or more and 100% or less of the tissue in a serum-free medium or serum-containing medium each containing a substance acting on the Wnt signal pathway and a substance inhibiting the FGF signal pathway for only a period before the appearance of a RPE65 gene-expressing cell, followed by culturing the resulting "cell aggregate in which a RPE65 gene-expressing cell does not appear" in a serum-free medium or serum-containing medium each free of a substance acting on the Wnt signal pathway. The "cell aggregate comprising a ciliary marginal zone-like structure" produced by the production method of the present invention is useful as a reagent for use for the evaluation of toxicity or drug efficacy of chemical substances and so on, or a material for use for the tests or treatments aiming at cell therapy and so on.

The "cell aggregate comprising a retinal tissue" to be used as a starting material in the production method of the present invention is a cell aggregate in which Chx10 positive cells are present in the retinal tissue in a proportion of 20% or more and 100% or less of the tissue. The aforementioned "proportion of Chx10 positive cells" is, for example, preferably 40% or more, more preferably 60% or more, particularly preferably 70% or more.

The "cell aggregate comprising a retinal tissue" to be used as a starting material in the production method of the present invention can be prepared, for example, from a pluripotent stem cell (preferably human pluripotent stem cell). As the pluripotent stem cell, embryonic stem cells and induced pluripotent stem cells can be mentioned.

The "cell aggregate comprising a retinal tissue" to be used as a starting material in the production method of the present invention can be specifically prepared, for example, by a method including the following steps (A) and (B):
(A) a step of subjecting pluripotent stem cells to floating culture in a serum-free medium to form an aggregate of pluripotent stem cells, and
(B) a step of performing floating culture of the aggregate formed in step (A) in a serum-free medium or serum-containing medium each free of a substance acting on the Sonic hedgehog signal transduction pathway and containing a substance acting on the BMP signal transduction pathway to give a cell aggregate comprising a retinal progenitor cell.

The step (A) for forming an aggregate of pluripotent stem cells by floating culture of pluripotent stem cells in a serum-free medium is explained.

The serum-free medium used in step (A) is not particularly limited as long as it is as mentioned above. For example, a serum-free medium supplemented with an appropriate amount of a commercially available serum replacement such as KSR and so on (e.g., medium of 1:1 mixture of IMDM and F-12 supplemented with 10% KSR, 450 μM 1-monothioglycerol and 1× Chemically Defined Lipid Concentrate) can be mentioned. The amount of KSR to be added to a serum-free medium in the case of human ES cells is generally about 1% to about 20%, preferably about 2% to about 20%.

The culture conditions such as culture temperature, $CO_2$ concentration and so on in step (A) can be appropriately determined. The culture temperature is, for example, about 30° C. to about 40° C., preferably about 37° C. The $CO_2$ concentration is, for example, about 1% to about 10%, preferably about 5%.

The concentration of the pluripotent stem cells in step (A) can be determined as appropriate to form aggregates of pluripotent stem cells more uniformly and efficiently. For example, when human ES cells are subjected to floating culture using a 96 well microwell plate, a liquid prepared to about $1\times10^3$ to about $1\times10^5$ cells, preferably about $3\times10^3$ to about $5\times10^4$ cells, more preferably about $5\times10^3$ to about $3\times10^4$ cells, most preferably about $1.2\times10^4$ cells, per well is added to the well, and the plate is left standing to form cell aggregates.

The time of floating culture necessary forming cell aggregates can be determined as appropriate according to the pluripotent stem cell to be used, so that the cells can be aggregated uniformly. To form uniform cell aggregates, it is desirably as short as possible. For example, in the case of human ES cells, aggregates are formed preferably within about for 24 hr, more preferably within about for 12 hr. The time for cell aggregate formation can be appropriately adjusted by controlling the tools for aggregating the cells, centrifugation conditions and so on.

Formation of aggregates of pluripotent stem cells can be determined based on the size and cell number of cell aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between cell aggregates, and so on.

The step (B) for obtaining a cell aggregate comprising a retinal progenitor cell by floating culture of the cell aggregate formed in step (A) in a serum-free medium or serum-containing medium each free of a substance acting on the Sonic hedgehog signal transduction pathway and containing a substance acting on the BMP signal transduction pathway is explained.

The medium to be used in step (B) is a serum-free medium or serum-containing medium not supplemented with a substance acting on the Sonic hedgehog signal transduction pathway and supplemented with a substance acting on the BMP signal transduction pathway, which does not require addition of a basement membrane preparation.

A serum-free medium or serum-containing medium to be used for such medium is not particularly limited as long as it is as mentioned above. For example, a serum-free medium supplemented with an appropriate amount of a commercially available serum replacement such as KSR and so on (e.g., medium of 1:1 mixture of IMDM and F-12 supplemented with 10% KSR, 450 µM 1-monothioglycerol and 1× Chemically Defined Lipid Concentrate) can be mentioned. The amount of KSR to be added to a serum-free medium in the case of human ES cells is generally about 1% to about 20%, preferably about 2% to about 20%.

As the serum-free medium to be used in step (B), the serum-free medium used in step (A) may be directly used, or may be replaced with a fresh serum-free medium. When the serum-free medium used in step (A) is directly used for step (B), a substance acting on the BMP signal transduction pathway may be added to the medium.

The substance acting on the Sonic hedgehog (hereinafter sometimes to be indicated as Shh) signal transduction pathway is a substance capable of enhancing signal transduction mediated by Shh. Examples of the substance acting on the Shh signal transduction pathway include protein belonging to the Hedgehog family (e.g., Shh), Shh receptor, Shh receptor agonist, Purmorphamine, or SAG and so on.

The substance acting on the BMP signal transduction pathway is a substance capable of enhancing signal transduction mediated by BMP. Examples of the substance acting on the BMP signal transduction pathway include BMP proteins such as BMP2, BMP4, BMP7 etc., GDF proteins such as GDF7 etc., anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd.

The concentration of a substance acting on the BMP signal transduction pathway only needs to be a concentration at which differentiation of the cells, that form an aggregate of pluripotent stem cells, into retinal cells can be induced. For example, in the case of BMP4, it is added to the medium to a concentration of about 0.01 nM to about 1 µM, preferably about 0.1 nM to about 100 nM, more preferably about 1.5 nM.

A substance acting on the BMP signal transduction pathway only needs to be added after about 24 hr from the start of the floating culture in step (A), and may be added to a medium within several days (e.g., within 15 days) from the start of the floating culture. Preferably, a substance acting on the BMP signal transduction pathway is added to a medium between day 1 and day 15, more preferably between day 1 and day 9, further preferably day 6, from the start of the floating culture.

After addition of a substance acting on the BMP signal transduction pathway to the medium, and after the start of the differentiation induction of the cells forming an aggregate of pluripotent stem cells into retinal cells, addition of the substance acting on the BMP signal transduction pathway to the medium is not necessary, and the medium may be exchanged with a serum-free medium or serum-containing medium each free of a substance acting on the BMP signal transduction pathway. In this way, the cost of medium can be suppressed. The cells that started differentiation induction into retinal cells can be confirmed by, for example, detecting the expression of Rax gene in the cells. The cell aggregate formed in step (A) by using pluripotent stem cells knocked-in with a fluorescence reporter protein gene such as GFP and so on into the Rax gene locus is subjected to floating culture in the presence of a substance acting on the BMP signal transduction pathway at a concentration necessary for differentiation induction into retinal cell, and fluorescence emitted from the expressed fluorescence reporter protein is detected, whereby the time period when differentiation induction into retinal cell was started can be confirmed. One embodiment of step (B) is a step for obtaining a cell aggregate comprising retinal progenitor cell, by floating culture of the cell aggregate formed in step (A) in a serum-free medium or serum-containing medium each free of a substance acting on the Sonic hedgehog signal transduction pathway but containing a substance acting on the BMP signal transduction pathway at a concentration necessary for differentiation induction into retinal cell, until a cell expressing Rax gene starts to appear.

The culture conditions such as culture temperature, $CO_2$ concentration and so on in step (B) can be appropriately determined. The culture temperature is, for example, about 30° C. to about 40° C., preferably about 37° C. The $CO_2$ concentration is, for example, about 1% to about 10%, preferably about 5%.

That a cell aggregate comprising a retinal progenitor cell was obtained can be confirmed by, for example, detecting the presence of a cell expressing Rax or PAX6, which is a retinal progenitor cell marker, in the aggregate. The "cell aggregate comprising a retinal progenitor cell" obtained by the method including above-mentioned steps (A) and (B) can be used as a "cell aggregate comprising a retinal tissue" as a starting material in the production method of the present invention.

The "cell aggregate comprising a retinal tissue" to be used as a starting material in the production method of the present invention can also be specifically prepared, for example, by a method including the following steps (C), (D) and (E):

(C) a step of subjecting pluripotent stem cells to floating culture in a serum-free medium containing a substance inhibiting the Wnt signal pathway to form an aggregate of pluripotent stem cells, (D) a step of subjecting the cell aggregate formed in step (C) to floating culture in a serum-free medium containing a basement membrane preparation, and (E) a step of subjecting the cell aggregate cultured in step (D) to floating culture in a serum-containing medium.

A substance inhibiting the Wnt signal pathway to be used in step (C) is not particularly limited as long as it can suppress signal transduction mediated by Wnt. Examples of the substance inhibiting the Wnt signal pathway include Dkk1, Cerberus protein, Wnt receptor inhibitor, soluble-type Wnt receptor, Wnt antibody, casein kinase inhibitor, dominant negative Wnt protein, CKI-7 (N-(2-aminoethyl)-5-chloro-isoquinoline-8-sulfonamide), D4476 (4-{4-(2,3-dihydrobenzo[1,4]dioxin-6-yl)-5-pyridin-2-yl-1H-imidazol-2-yl}benzamide), IWR-1-endo (IWR1e), IWP-2 and so on. The concentration of the substance inhibiting the Wnt signal pathway only needs to be a concentration at which aggregates of pluripotent stem cells are formed. For example, a common substance inhibiting the Wnt signal pathway such as IWR1e is added at a concentration of about 0.1 µM to about 100 µM, preferably about 1 µM to about 10 µM, more preferably around 3 µM.

A substance inhibiting the Wnt signal pathway may be added to serum-free medium before the start of the floating culture, or added to a serum-free medium within several days from the start of the floating culture (e.g., within 5 days). Preferably, a substance inhibiting the Wnt signal pathway is added to a serum-free medium within 5 days, more preferably within 3 days, from the start of the floating culture, most preferably simultaneously with the start of the floating culture. In addition, floating culture is performed up to day 18, more preferably day 12, from the start of the floating culture with the addition of a substance inhibiting the Wnt signal pathway.

The culture conditions such as culture temperature, and $CO_2$ concentration in step (C) can be appropriately determined. While the culture temperature is not particularly limited, it is, for example, about 30° C. to about 40° C., preferably around about 37° C. The $CO_2$ concentration is, for example, about 1% to about 10%, preferably around about 5%.

The concentration of the pluripotent stem cells in step (C) can be determined as appropriate by those of ordinary skill in the art to form aggregates of pluripotent stem cells more uniformly and efficiently. The concentration of the pluripotent stem cells when forming cell aggregates is not particularly limited as long as it permits formation of uniform aggregates of stem cells. For example, when human ES cells are subjected to floating culture using a 96 well microwell plate, a liquid prepared to about $1 \times 10^3$ to about $5 \times 10^4$ cells, preferably about $3 \times 10^3$ cells to about $3 \times 10^4$ cells, more preferably about $5 \times 10^3$ cells to about $2 \times 10^4$ cells, most preferably around $9 \times 10^3$ cells, per well is added, and the plate is left standing to form cell aggregates.

The time of floating culture necessary forming cell aggregates can be determined as appropriate according to the pluripotent stem cell to be used, as long as the cells can be aggregated rapidly. To form uniform cell aggregates, it is desirably as short as possible. For example, in the case of human ES cells, cell aggregates are desirably formed preferably within for 24 hr, more preferably within for 12 hr. The time for cell aggregate formation can be appropriately adjusted by those of ordinary skill in the art by controlling the tools for aggregating the cells, centrifugation conditions and so on.

Those of ordinary skill in the art can determine whether cell aggregates of pluripotent stem cells have been formed, based on the size and cell number of cell aggregates, macroscopic morphology, microscopic morphology by tissue staining analysis and uniformity thereof, expression of differentiation and undifferentiation markers and uniformity thereof, control of expression of differentiation marker and synchronism thereof, reproducibility of differentiation efficiency between cell aggregates, and so on.

The basement membrane preparation to be used in step (D) refers to one containing basement membrane-constituting components having a function to control cell morphology, differentiation, growth, motility, expression of function and so on which are similar to those of epithelial cell, when intended cells capable of forming a basement membrane are plated thereon and cultured. Here, the "basement membrane constituting component" refers to an extracellular matrix molecule in the morphology of a thin membrane present between epithelial cell layer and interstitial cell layer and so on in animal tissues. A basement membrane preparation can be produced by, for example, removing cells capable of forming a basement membrane, which adhere onto a support via a basement membrane, with a solution capable of dissolving the lipid of the cells, an alkali solution and so on. Examples of preferable basement membrane preparation include products commercially available as basement membrane components (e.g., Matrigel™ (manufactured by Becton, Dickinson and Company: hereinafter, sometimes referred to as Matrigel)), and extracellular matrix molecules known as basement membrane components (e.g., laminin, type IV collagen, heparan sulfate proteoglycan, entactin and so on).

Matrigel™ is a product prepared from a basement membrane derived from Engelbreth Holm Swarn (EHS) mouse sarcoma. The main component of Matrigel™ is type IV collagen, laminin, heparan sulfate proteoglycan, and entactin. In addition to these, TGF-β, fibroblast growth factor (FGF), tissue plasminogen activator, and a growth factor naturally produced by EHS tumor are contained. The "growth factor reduced (GFR) product" of Matrigel™ has a lower growth factor concentration than common Matrigel™. In the present invention, GFR product is preferably used.

While the concentration of the basement membrane preparation to be added to a serum-free medium for the floating culture in step (D) is not particularly limited as long as the epithelial structure of the neural tissue (e.g., retinal tissue) is stably maintained, for example, it is preferably 1/20 to 1/200 volume, more preferably around 1/100 volume, of the culture medium when Martigel™ is used. While basement membrane preparation may already have been added to the medium when the culture of stem cell is started, it is preferably added to the serum-free medium within 5 days, more preferably within 2 days, from the start of the floating culture.

As the serum-free medium to be used in step (D), the serum-free medium used in the step (C) may be directly used, or may be replaced with a fresh serum-free medium.

When the serum-free medium used in the step (C) is directly used for this step, the "basement membrane preparation" can be added to the medium.

The culture conditions such as culture temperature, and $CO_2$ concentration in step (D) can be appropriately determined. While the culture temperature is not particularly limited, it is, for example, about 30° C. to about 40° C., preferably around about 37° C. The $CO_2$ concentration is, for example, about 1% to about 10%, preferably around about 5%.

As the serum-containing medium to be used in step (E), may be used the serum-free medium used in the culture of step (D) to which a serum is directly added, or one replaced with a fresh serum-containing medium.

The serum is added on or after day 7, more preferably on or after day 9, most preferably on day 12, from the start of the floating culture. The concentration of the serum to be added is about 1% to about 30%, preferably about 3% to about 20%, more preferably around 10%.

In step (E), the production efficiency of retinal tissue can be increased by adding a substance acting on the Shh signal pathway in addition to the serum.

The substance acting on the Shh signal pathway is not m particularly limited as long as it can enhance signal transduction mediated by Shh. Examples of the substance acting on the Shh signal pathway include proteins belonging to the Hedgehog family (e.g., Shh), Shh receptor, Shh receptor agonist, Purmorphamine, SAG and so on.

The concentration of the substance acting on the Shh signal pathway used in this step is, for example, in the case of common substance acting on the Shh signal pathway such as SAG, about 0.1 nM to about 10 µM, preferably about 10 nM to about 1 µM, more preferably around 100 nM.

In the thus-cultured cell aggregates, the retinal tissue is present to cover the surface of the cell aggregate. The retinal tissue can be confirmed by immunostaining method and so on. The cell aggregate obtained by the above-mentioned method including steps (C), (D) and (E) can be used as a "cell aggregate comprising a retinal tissue" to be a starting material in the production method of the present invention.

The presence of a retinal tissue in the cell aggregate obtained by the above-mentioned method including steps (A) and (B) or the above-mentioned method including steps (C), (D) and (E) can also be confirmed as follows. For example, the cell aggregates obtained by the above-mentioned method are subjected to floating culture in a serum-containing medium. Examples of the cell culture vessel to be used for floating culture include those mentioned above. The culture conditions such as culture temperature, $CO_2$ concentration, and $O_2$ concentration of the floating culture can be appropriately determined. While the culture temperature is not particularly limited, it is, for example, about 30° C. to about 40° C., preferably about 37° C. The $CO_2$ concentration is, for example, about 1% to about 10%, preferably about 5%. The $O_2$ concentration is, for example, about 20% to about 70%, preferably about 20% to about 60%, more preferably about 30% to about 50%. While the culture period is not particularly limited, it is generally for 48 hr or more, preferably 7 days or more.

After completion of the floating culture, the cell aggregates are fixed with a fixative such as para-formaldehyde solution and so on, and a cryosection is prepared. The obtained cryosection is immunostained, and formation of a layer structure of retinal tissue is confirmed. Since respective layers of a retinal tissue are composed of different retinal progenitor cells (photoreceptor, horizontal cell, bipolar cell, amacrine cell, retinal ganglion cell), formation of a layer structure can be confirmed by immunostaining using antibodies against the aforementioned markers expressed in these cells.

The "proportion of Chx10 positive cells" in a retinal tissue contained in the cell aggregate prepared as mentioned above can be examined by, for example, the following method.

(1) First, a cryosection of "a cell aggregate comprising a retinal tissue" is prepared.

(2) Then, immunostaining of Rax protein is performed. When a gene recombinant cell obtained by altering a Rax gene-expressing cell to express a fluorescence protein such as GFP is used, the expression of the aforementioned fluorescence protein, is observed using a fluorescence microscope and so on. A retinal tissue region expressing Rax gene is specified in the obtained immunostained images or fluorescence microscopic images.

(3) Using the same section as the cryosection wherein the retinal tissue region expressing Rax gene has been specified or an adjacent section as a sample, the nucleus is stained with a nuclear staining reagent such as DAPI. Then, the number of stained nuclei in the above-specified retinal tissue region expressing Rax gene is counted, whereby the number of the cells in the retinal tissue region is measured.

(4) Using the same section as the cryosection wherein the retinal tissue region expressing Rax gene has been specified or an adjacent section as a sample, Chx10 protein is immunostained. The number of Chx10 positive cells in the above-specified retinal tissue region is counted.

(5) Based on each number of nuclei measured in the above-mentioned (3) and (4), the number of nuclei in Chx10 positive cells is divided by the number of nuclei in the above-specified retinal tissue region expressing the Rax gene, whereby the "proportion of Chx10 positive cells" is calculated.

In the production method of the present invention, firstly, a cell aggregate comprising a retinal tissue in which Chx10 positive cells are present in a proportion of 20% or more and 100% or less of the tissue is cultured in a serum-free medium or serum-containing medium each containing a substance acting on the Wnt signal pathway and a substance inhibiting the FGF signal pathway for only a period before the appearance of a RPE65 gene-expressing cell.

As a preferable culture here, floating culture can be mentioned.

As a serum-free medium, a serum-free medium which is a basal medium supplemented with N2 or KSR can be mentioned. More specifically, a serum-free medium which is a DMEM/F-12 medium supplemented with N2 supplement (N2, Invitrogen) can be mentioned. As the serum-containing medium, a serum-containing medium which is a basal medium supplemented with fetal bovine serum can be mentioned.

The culture conditions such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

The substance acting on the Wnt signal pathway to be contained in a serum-free medium or serum-containing medium when the above-mentioned "cell aggregate comprising a retinal tissue" is cultured in the medium is not particularly limited as long as it can enhance signal transduction mediated by Wnt. Specific examples of the substance acting on the Wnt signal pathway include protein belonging to Wnt family (e.g., Wnt3a), Wnt receptor, Wnt receptor agonist, GSK3β inhibitor (e.g., 6-Bromoindirubin-3'-oxime (BIO), CHIR99021, Kenpaullone) and so on.

The concentration of the substance acting on the Wnt signal pathway to be contained in a serum-free medium or serum-containing medium in the case of a common substance acting on the Wnt signal pathway such as CHIR99021 is, for example, in the range of about 0.1 µM to about 100 µM, preferably, for example, in the range of about 1 µM to about 30 µM, more preferably, for example, around 3 µM.

The substance inhibiting the FGF signal pathway to be contained in a serum-free medium or serum-containing medium when the above-mentioned "cell aggregate comprising a retinal tissue" is cultured in the medium is not particularly limited as long as it can inhibit signal transduction mediated by FGF. Examples of the substance inhibiting FGF signal pathway include FGF receptor, FGF receptor inhibitor (e.g, SU-5402, AZD4547, BGJ398), MAP kinase cascade inhibitory substance (e.g., MEK inhibitor, MAPK inhibitor, ERK inhibitor), PI3 kinase inhibitor, Akt inhibitor and so on.

The concentration of a substance inhibiting FGF signal pathway contained in a serum-free medium or serum medium only needs to be a concentration at which differentiation of the cells, that form an aggregate of pluripotent stem cells, into retinal cells can be induced. For example, in the case of SU-5402, it is added to the medium to a concentration of about 0.1 µM to about 100 µM, preferably about 1 µM to about 30 µM, more preferably about 5 µM.

"Culturing for only a period before the appearance of a RPE65 gene-expressing cell" in the production method of the present invention means culturing in the whole or a part of the period before the appearance of a RPE65 gene-expressing cell. That is, culturing in the whole or a part of the period (any period) during which the "cell aggregate comprising a retinal tissue" in the culture system is constituted by cells that do not substantially express RPE65 gene suffices. By employing such culturing, a cell aggregate in which a RPE65 gene-expressing cell does not appear can be obtained. The "cell aggregate in which a RPE65 gene-expressing cell does not appear" includes a "cell aggregate in which a RPE65 gene-expressing cell does not appear at all" and "cell aggregate in which a RPE65 gene-expressing cell does not appear substantially". As the "cell aggregate in which a RPE65 gene-expressing cell does not appear substantially", a cell aggregate containing RPE65 positive cells at a ratio of about 1% or less in the retinal tissue contained in the cell aggregate can be mentioned.

To determine such particular period, the "cell aggregate comprising a retinal tissue" is used as a sample, and the presence or absence of expression of RPE65 gene contained in the sample only needs to be measured by a general genetic engineering method or a biochemical method. Specifically, for example, the presence or absence of expression of RPE65 gene or the level thereof can be examined by subjecting a cryosection of the aforementioned "cell aggregate comprising a retinal tissue" to an immunostaining method using an antibody against RPE65 protein.

A "period before the appearance of a RPE65 gene-expressing cell" is, for example, a period during which the ratio of Chx10 positive cells present in the above-mentioned retinal tissue decreases than that at the time of start of the culture of the aforementioned cell aggregate in a serum-free medium or serum-containing medium each containing a substance acting on the Wnt signal pathway and a substance inhibiting FGF signal pathway, and falls within the range of 30% to 0%. The "cell aggregate in which a RPE65 gene-expressing cell does not appear" is a cell aggregate in which Chx10 positive cells are present in the above-mentioned retinal tissue in a proportion of within 30% to 0% of the tissue.

While the number of days of the "period before the appearance of a RPE65 gene-expressing cell" varies depending on the kind of the substance acting on the Wnt signal pathway and the substance inhibiting the FGF signal pathway, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 3 days to 6 days. When a serum-containing medium (e.g., serum-containing medium which is a basal medium supplemented with fetal bovine serum) is used, the aforementioned period is preferably, for example, within 12 days, more preferably, for example, 6 days to 9 days.

Then the "cell aggregate in which a RPE65 gene-expressing cell does not appear" obtained by culturing as mentioned above is cultured in a serum-free medium or serum-containing medium each free a substance acting on the Wnt signal pathway.

As a preferable culture here, floating culture can be mentioned.

As the serum-free medium, a medium which is a basal medium supplemented with N2 or KSR can be mentioned. As the serum-containing medium, a medium which is a basal medium supplemented with fetal bovine serum can be mentioned. More specifically, a serum medium which is a DMEM/F-12 medium supplemented with fetal bovine serum can be mentioned.

The aforementioned serum-free medium or serum-containing medium may contain a known growth factor, an additive and a chemical substance that promote the growth, and so on. Examples of the known growth factor include EGF, FGF, IGF, insulin and so on. Examples of the additive that promotes the growth include N2 supplement (N2, Invitrogen), B27 supplement (Invitrogen), KSR and so on. Examples of the chemical substance that promotes the growth include retinoids (e.g., retinoic acid) and taurine.

A preferable culture period is, for example, a culture period during which the ratio of Chx10 positive cells present in the above-mentioned retinal tissue increases than that at the time of start of the culture of the aforementioned cell aggregate in a serum-free medium or serum-containing medium each free a substance acting on the Wnt signal pathway, and reaches 30% or more.

The culture conditions such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

While the number of the above-mentioned culture days until "a cell aggregate comprising a ciliary marginal zone-like structure" is obtained varies depending on the kind of the serum-free medium or serum-containing medium, other culture conditions and so on, it is, for example, within 100 days. The aforementioned number of culture days is preferably, for example, 20 days to 70 days, more preferably, for example, 30 days to 60 days.

In the thus-produced "cell aggregate comprising a ciliary marginal zone-like structure", a retinal pigment epithelium and a retinal tissue (specifically, neural retina) are present adjacent to the ciliary marginal zone-like structure in the same cell aggregate. The structure can be confirmed by microscopic observation and so on. Specifically, for example, when a cell aggregate is produced from pluripotent stem cells wherein GFP gene is knocked into Rax gene locus (RAX::GFP knock-in cell), the presence of neural retina which is RAX::GFP strong positive region, retinal pigment epithelium which is an epithelial tissue in which pigmentation can be observed with transmitted light and, a ciliary marginal zone-like structure in a boundary region between neural retina and retinal pigment epithelium and having a characteristic structure can be confirmed by using a fluorescence stereoscopic microscope (e.g., SZX16 manufactured by Olympus Corporation).

In the thus-produced "cell aggregate comprising a ciliary marginal zone-like structure", a ciliary marginal zone-like structure is formed in a region between two neural retinal tissues. That is, a tissue continuously containing a neural retinal tissue, a ciliary marginal zone-like structure and another neural retinal tissue is sometimes formed. In this case, the presence of a ciliary marginal zone-like structure can be confirmed by microscopic observation since the ciliary marginal zone-like structure is characteristically thinner than the adjacent neural retinal tissue.

A highly pure retinal tissue (specifically, neural retina) can be prepared by physically cutting out a retinal tissue (specifically, neural retina) from the aforementioned "cell aggregate comprising a ciliary marginal zone-like structure" with tweezers etc. A highly pure retinal tissue (specifically, neural retina) can be further continuously cultured (specifically, long-term culture for, for example, 60 days or longer) while maintaining the good tissue structure it has. The culture conditions such as culture temperature, $CO_2$ concentration, $O_2$ concentration can be those generally used for tissue culture. In this case, culture may be performed in the presence of a serum, a known growth factor, an additive and a chemical substance that promote the growth, and so on. Examples of the known growth factor include EGF, FGF and so on. Examples of the additive that promotes the growth include N2 supplement (Invitrogen), B27 supplement (Invitrogen) and so on.

The present invention also includes use of a cell aggregate comprising a ciliary marginal zone-like structure produced by the production method of the present invention as a reagent for the evaluation of the toxicity or drug efficacy, use of a cell aggregate comprising a ciliary marginal zone-like structure produced by the production method of the present invention as a biological material for transplantation and so on.

<Use of Cell Aggregate Comprising Ciliary Marginal Zone-Like Structure as Reagent for Evaluating Toxicity or Drug Efficacy>

The cell aggregate comprising a ciliary marginal zone-like structure produced by the production method of the present invention can be used for screening for a therapeutic drug for a disease caused by a disorder of retinal cell, a material for the study of diseases or a drug discovery material. The cell aggregate comprising a ciliary marginal zone-like structure produced by the production method of the present invention is also utilizable for the evaluation of the toxicity or drug efficacy of a chemical substance and so on, as well as study of toxicity such as phototoxicity, neurotoxicity and so on, toxicity test and soon. For example, a cell aggregate comprising a ciliary marginal zone-like structure produced by the production method of the present invention is brought into contact with a test substance, and an influence of the substance on the cell or the tissue is assayed, based on which the toxicity or drug efficacy of the substance is evaluated.

<Use of Cell Aggregate Comprising Ciliary Marginal Zone-Like Structure as Biological Material for Transplantation>

The cell aggregate comprising a ciliary marginal zone-like structure produced by the production method of the present invention can be used as a biological material for transplantation used for supplementing a disordered tissue itself in a cell damage state (e.g., used for transplantation operation) and so on. For example, an effective amount of a cell aggregate comprising a ciliary marginal zone-like structure, which is produced by the production method of the present invention, is transplanted to a subject in need of the transplantation, whereby a disease due to a disorder of retinal tissue is treated.

EXAMPLES

The present invention is explained in more detail in the following by referring to Examples, which are not to be construed as limitative.

Example 1 (Production Example of Cell Aggregate Comprising Retinal Tissue Using Human ES Cell)

RAX::GFP knock-in human ES cells (derived from KhES-1; Nakano, T. et al. Cell Stem Cell 2012, 10(6), 771-785) were cultured according to the methods described in "Ueno, M. et al. PNAS 2006, 103(25), 9554-9559" and "Watanabe, K. et al. Nat Biotech 2007, 25, 681-686". As the medium, DMEM/F12 medium (Sigma) supplemented with 20% KSR (Knockout Serum™ Replacement; Invitrogen), 0.1 mM 2-mercaptoethanol, 2 mM L-glutamine, 1× non-essential amino acid and 8 ng/ml bFGF was used. The aforementioned cultured ES cells were singly dispersed in TrypLE Express (Invitrogen), and the singly dispersed ES cells were floated in a 100 µl serum-free medium to $1.2 \times 10^4$ cells per well of a non-cell adhesive 96-well culture plate (SUMILON spheroid plate, SUMITOMO BAKELITE CO., LTD.) to allow for rapid formation of an aggregate, which was subjected to floating culture at 37° C., 5% $CO_2$. The serum-free medium used then was a serum-free medium which was a 1:1 mixture of F-12 medium and IMDM medium added with 10% KSR, 450 µM 1-monothioglycerol, 1× Chemically Defined Lipid Concentrate, 20 µM Y27632. BMP4 was added at a final concentration of 1.5 nM on day 6 from the start of the floating culture, and the floating culture was continued. A half amount of the culture medium in the well was exchanged every 3 days with the above-mentioned medium free of a substance acting on the BMP signal transduction pathway.

Figure 1:
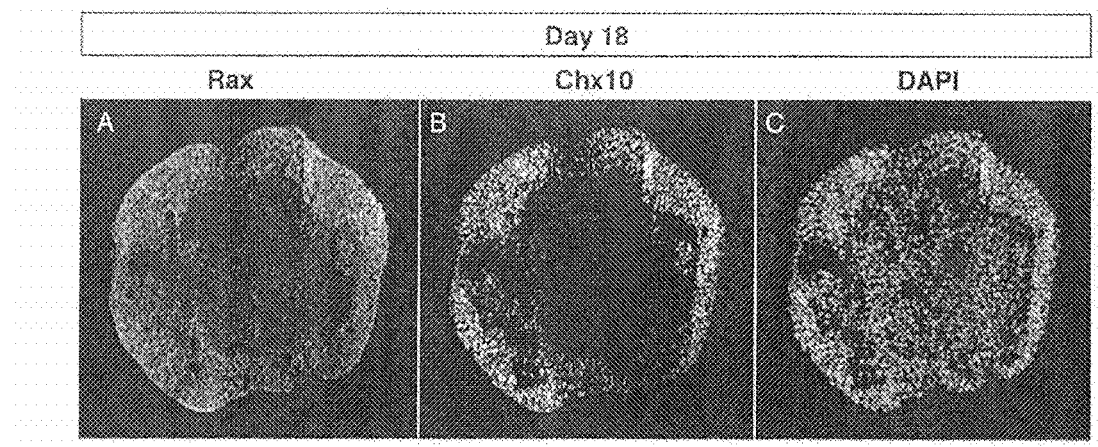
FIG. 1 shows stained images of a cryosection of cell aggregates containing a retinal tissue (on day 18 from the start of the floating culture). "A" is a GFP fluorescence image of Rax gene-expressing cell, "B" is an immunostained image of the Chx10 positive cell, and "C" is a DAPI stained image of the cell nucleus.

The thus-produced cell aggregate on day 18 from the start of the floating culture was fixed with 4% para-formaldehyde to prepare a cryosection. The prepared cryosection was subjected to fluorescence microscopic observation of a GFP fluorescence image (FIG. 1A), immunostaining with Chx10 which is one of neural retinal progenitor cell markers (FIG. 1B) or DAPI staining for staining of cell nucleus (FIG. 1C). From the comparison of FIG. 1A showing the presence of the whole retinal tissue cells, and FIG. 1B showing the presence of Chx10 positive cell, the retinal tissue contained in the cell aggregate produced as mentioned above contained Chx10 positive cells in about 80% of the tissue (see FIG. 1).

Comparative Example 1 (Culture of Cell Aggregate Comprising Retinal Tissue in Serum-Containing Medium Free a Substance Acting on Wnt Signal Pathway and a Substance Inhibiting FGF Signal Pathway)

A cell aggregate comprising a retinal tissue on day 18 from the start of the floating culture, which was produced by the method described in Example 1, was subjected to floating culture in a serum-containing medium free a substance acting on the Wnt signal pathway and a substance inhibiting FGF signal pathway (medium which was DMEM/F-12 medium supplemented with 10% fetal bovine serum, 1% N2 supplement, 0.5 µM retinoic acid, and 100 µM taurine) for 6 days, i.e., up to day 24 from the start of the floating culture (FIG. 2A,B), or 17 days, i.e., up to day 35 from the start of the floating culture (FIG. 2C,D).

The obtained cell aggregate was fixed with 4% paraformaldehyde to prepare a cryosection. The prepared cryosection was subjected to immunostaining with Chx10 which is one of the neural retinal progenitor cell markers (FIG. 2A,C), or immunostaining with MITF which is one of the retinal pigment epithelial cell markers (FIG. 2B,D). It was found that about 80% of the retinal tissue contained in the cell aggregate were Chx10 positive cells (FIG. 2A,C), and the ratio of MITF positive cells present therein was not more than 3% (FIG. 2B,D), both on day 24 from the start of the floating culture and on day 35 from the start of the floating culture.

Example 2 (Culture of Cell Aggregate Comprising Retinal Tissue in Serum-Free Medium Containing a Substance Acting on Wnt Signal Pathway and a Substance Inhibiting FGF Signal Pathway)

A cell aggregate comprising a retinal tissue on day 18 from the start of the floating culture, which was produced by the method described in Example 1, was subjected to floating culture in a serum-free medium (medium which was DMEM/F-12 medium supplemented with 1% N2 supplement) containing a substance acting on the Wnt signal pathway (3 µM CHIR99021) and a substance inhibiting FGF signal pathway (5 µM SU5402) for 6 days, i.e., up to day 24 from the start of the floating culture (FIG. 3A,B) and further in a serum-containing medium (medium which was DMEM/F-12 medium supplemented with 1% fetal calf serum and 1% N2 supplement) containing a substance acting on the Wnt signal pathway (3 µM CHIR99021) and free of a substance inhibiting FGF signal pathway for 11 days, i.e., up to day 35 from the start of the floating culture (FIG. 3C,D).

The obtained cell aggregate was fixed with 4% paraformaldehyde to prepare a cryosection. The prepared cryosection was subjected to immunostaining with Chx10 which is one of the neural retinal progenitor cell markers (FIG. 3A,C), or immunostaining with MITF which is one of the retinal pigment epithelial cell markers (FIG. 3B,D). It was found that about 80% of the retinal tissue contained in the cell aggregate were MITF positive cells (FIG. 3B,D), and the ratio of Chx10 positive cells present therein was not more than 3% (FIG. 3A,C), both on day 24 from the start of the floating culture and on day 35 from the start of the floating culture. The cell aggregate on day 24 from the start of the floating culture did not show appearance of a RPE65 gene-expressing cell.

Figure 2:
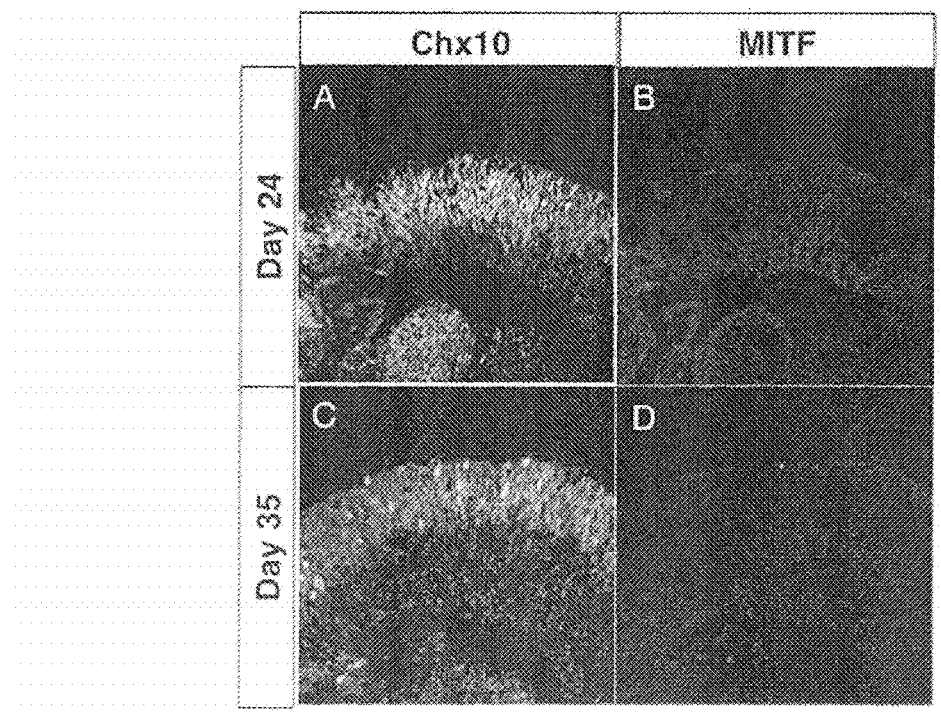
FIG. 2 shows stained images of a cryosection of cell aggregates obtained by floating culture of cell aggregates containing a retinal tissue (on day 18 from the start of the floating culture) in a serum medium free of a substance acting on the Wnt signal pathway and a substance inhibiting FGF signal pathway for 6 days, i.e., up to day 24 from the start of the floating culture (A,B), or 17 days, i.e., up to day 35 from the start of the floating culture (C,D). "A" and "C"

From the comparison of FIG. 2 and FIG. 3, it was suggested that fate conversion of Chx10 positive neural retina to MITF positive retinal pigment epithelium (RPE)-like tissue occurred in the retinal tissue contained in the cell aggregate, due to the culture operation in a serum-free medium containing a substance acting on the Wnt signal pathway and a substance inhibiting FGF signal pathway.

Example 3 (Floating Culture of "Cell Aggregate in which a RPE65 Gene-Expressing Cell does not Appear" in Serum-Containing Medium Free of Substance Acting on the Wnt Signal Pathway"—1)

A cell aggregate comprising a retinal tissue on day 24 from the start of the floating culture, which was produced by the method described in Example 2, was subjected to floating culture in a serum-containing medium (medium which is DMEM/F-12 medium supplemented with 10% fetal bovine serum, 1% N2 supplement, 0.5 µM retinoic acid, and 100 µM taurine) free of a substance acting on the Wnt signal pathway and a substance inhibiting FGF signal pathway further for 11 days, i.e., up to day 35 from the start of the floating culture, or 39 days, i.e., up to day 63 from the start of the floating culture under 40% $O_2$ conditions, and the obtained cell aggregate was fixed with 4% para-formaldehyde to prepare a cryosection.

The cryosections prepared from the cell aggregates on day 24 from the start of the floating culture (FIG. 4A,B), and cell aggregates on day 35 (FIG. 4C,D) were subjected to immunostaining with Chx10 (FIG. 4A,C), and immunostaining with MITF (FIG. 4B,D). It was found that retinal tissues contained in the cell aggregate on day 24 from the start of the floating culture have retinal pigment epithelial-like properties, since, on day 24 from the start of the floating culture, about 80% of the retinal tissue contained in the cell aggregate were MITF positive cells (FIG. 4B), and the ratio of Chx10 positive cells present therein was not more than 3% (FIG. 4A). The cell aggregate on day 24 from the start of the floating culture did not show appearance of a RPE65 gene-expressing cell. It was found that retinal tissues contained in the cell aggregate on day 35 from the start of the floating culture have properties of Chx10 positive neural retina, since, on day 35 from the start of the floating culture, about 80% of the retinal tissue contained in the cell aggregate were Chx10 positive cells (FIG. 4C), and the ratio of MITF positive cells present therein was not more than 3% (FIG. 4D). A comparison of FIG. 3 and FIG. 4 suggests that fate conversion from retinal pigment epithelial-like tissue to neural retina-like tissue occurred in retinal tissues contained in the cell aggregate between day 24 and day 35 from the start of the floating culture.

The cryosections (FIG. 5A,B,C) prepared from the cell aggregate on day 63 from the start of the floating culture were subjected to fluorescence microscopic observation of Rax::GFP fluorescence immunostaining images (FIG. 5A), immunostaining with Otx1 which is one of ciliary marginal zone markers (FIG. 5B), or immunostaining with Rdh10 which is one of ciliary marginal zone markers (FIG. 5C). A comparison of FIG. 5A,B reveals that a part of Rax positive neural retina is Otx1 co-positive, and it is clear from FIG. 5C that Rdh10 positive cell is present. In the manner mentioned above, it could be confirmed in the cell aggregate after floating culture for 39 days in a serum-containing medium free of a substance acting on the Wnt signal pathway that the cells positive to staining with either one or both of Otx1 and Rdh10 (that is, cells expressing either one or both of Otx1 and Rdh10 genes which is a marker gene of ciliary marginal zone-like structure) were present as a nearly-uniform group region in the tissue present in the boundary region of retinal tissue (specifically, neural retina) and retinal pigment epithelium (see FIG. 5B,C), and a cell aggregate comprising a ciliary marginal zone-like structure was produced with high efficiency.

Example 4 (Floating Culture of "Cell Aggregate in which a RPE65 Gene-Expressing Cell does not Appear" in Serum-Containing Medium Free of a Substance Acting on the Wnt Signal Pathway"—2)

Cell aggregates comprising a retinal tissue were each subjected to floating culture under the following three conditions, and cell aggregates on day 35 from the start of the floating culture were prepared.
(culture conditions A) A cell aggregate comprising a retinal tissue on day 18 from the start of the floating culture, which was produced by the method described in Example 1, was subjected to floating culture in a serum-containing medium (medium which is DMEM/F-12 medium supplemented with 10% fetal bovine serum, 1% N2 supplement, 0.5 μM retinoic acid, and 100 μM taurine) free of a substance acting on the Wnt signal pathway and a substance inhibiting FGF signal pathway for 17 days, i.e., up to day 35 from the start of the floating culture (FIG. 6A).

(culture conditions B) A cell aggregate comprising a retinal tissue on day 18 from the start of the floating culture, which was produced by the method described in Example 1, was subjected to floating culture in a serum-free medium (medium which is DMEM/F12 medium supplemented with 1% N2 supplement) containing a substance acting on the Wnt signal pathway (3 μM CHIR99021) and a substance inhibiting FGF signal pathway (5 μM SU5402) for 3 days, i.e., up to day 21 from the start of the floating culture. The cell aggregate on day 21 from the start of the floating culture did not show appearance of a RPE65 gene-expressing cell. Furthermore, the cell aggregate on day 21 from the start of the floating culture was subjected to floating culture in a serum-containing medium (medium which was DMEM/F-12 medium supplemented with 10% fetal bovine serum, 1% N2 supplement, 0.5 μM retinoic acid, and 100 μM taurine) free of a substance acting on the Wnt signal pathway and a substance inhibiting FGF signal pathway for 14 days, i.e., up to day 35 from the start of the floating culture (FIG. 6B).

(culture conditions C) A cell aggregate comprising a retinal tissue on day 18 from the start of the floating culture, which was produced by the method described in Example 1, was subjected to floating culture in a serum-free medium (medium which is DMEM/F12 medium supplemented with 1% N2 supplement) containing a substance acting on the Wnt signal pathway (3 μM CHIR99021) and a substance inhibiting FGF signal pathway (5 μM SU5402) for 5 days, i.e., up to day 23 from the start of the floating culture. The cell aggregate on day 23 from the start of the floating culture did not show appearance of a RPE65 gene-expressing cell. Furthermore, the cell aggregate on day 23 from the start of the floating culture was subjected to floating culture in a serum-containing medium (medium which was DMEM/F-12 medium supplemented with 10% fetal bovine serum, 1% N2 supplement, 0.5 μM retinoic acid, and 100 μM taurine) free of a substance acting on the Wnt signal pathway and a substance inhibiting FGF signal pathway for 12 days, i.e., up to day 35 from the start of the floating culture (FIG. 6B).

The obtained cell aggregates on day 35 from the start of the floating culture were each observed under a fluorescence stereoscopic microscope (SZX16 manufactured by Olympus Corporation). The presence or absence of neural retina which is RAX::GFP strong positive region, retinal pigment epithelium which is an epithelial tissue in which pigmentation can be observed with transmitted light and, a ciliary marginal zone-like structure in a boundary region between neural retina and retinal pigment epithelium and having a characteristic structure was observed, and the proportion of a cell aggregate containing neural retina alone (FIG. 6, gray bar graph), proportion of a cell aggregate containing neural retina formed continuously from the ciliary marginal zone-like structure (FIG. 6, black bar graph), and proportion of a cell aggregate containing free of neural retina and containing retinal pigment epithelium and other tissues (FIG. 6, white bar graph) were examined.

As a result, the proportion of aggregate mass containing neural retina formed continuously from the ciliary marginal zone-like structure was not more than 3% under culture conditions A, and increased to 30% under culture conditions B and 39% under culture conditions C in the production method of the present invention.

Example 5 (Culture of Cell Aggregate Comprising Retinal Tissue in Serum-Free Medium Containing a Substance Acting on Wnt Signal Pathway and a Substance Inhibiting FGF Signal Pathway)

A cell aggregate comprising a retinal tissue on day 18 from the start of the floating culture, which was produced by the method described in Example 1, was subjected to floating culture in a serum-free medium (medium which is DMEM/F-12 medium supplemented with 1% N2 supplement) containing a substance acting on the Wnt signal pathway (3 μM CHIR99021) and a substance inhibiting FGF signal pathway (5 μM SU5402) for 6 days, i.e., up to day 24 from the start of the floating culture.

The obtained cell aggregate was fixed with 4% paraformaldehyde to prepare a cryosection. The prepared cryosections were subjected to DAPI staining for staining of cell nucleus (FIG. 7A), immunostaining with RPE65 which is one of the mature retinal pigment epithelial cell markers (FIG. 7B), and immunostaining with Mitf which is one of the retinal pigment epithelial cell markers. It was found that the proportion of RPE65 positive cells present in the retinal tissue contained in the cell aggregate was not more than 1% on day 24 from the start of the floating culture (FIG. 7A,B). In this case, about 80% of the retinal tissues contained in the cell aggregate were MITF positive cells.

Reference Example 1

Production Example of Cell Aggregate Comprising Retinal Tissue by Using Induced Pluripotent Stem Cells (iPS Cells)

Human iPS cell line 201B7 (available from Incorporated Administrative Agency RIKEN BioResource Center or iPS Academia Japan, Inc.) is cultivated according to the methods described in "Ueno, M. et al. PNAS 2006, 103(25), 9554-9559", "Watanabe, K. et al. Nat Biotech 2007, 25, 681-686". As the medium, a medium which is DMEM/F-12 medium (Siyma) supplemented with 20% KSR (Knockout™ Serum Replacement; Invitrogen), 0.1 mM 2-mercaptoethanol, 2 mM L-glutamine, 1× non-essential amino acid, 5 ng/ml bFGF is used. The aforementioned cultured iPS cells were singly dispersed using TrypLE Express (Invitrogen), suspended in 100 μl of serum-free medium at $1.2 \times 10^4$ cells per well of a non-cell adhesive 96 well culture plate (SUMILON spheroid pfaes, SUMITOMO BAKELITE), and floating culture is performed at 37° C., 5% $CO_2$. As the serum-free medium, a serum-free medium which is a 1:1 mixture of F-12 medium and IMDM medium supplemented with 10% KSR, 450 μM 1-monothioglycerol, 1× Chemically Defined Lipid Concentrate, 20 μM Y27632 is used. At some time point between day 1 and day 15 from the start of the floating culture, any of human recombinant BMP4 (R&D) at final concentration of 1.5 nM, BMP2 (R&D) at final concentration of 100 ng/ml, BMP7 (R&D) at final concentration of 100 ng/ml, and GDF7 (R&D) at final concentration of 100 ng/ml was added and floating culture is performed. A half amount of the culture medium in the well is exchanged every 3 days with the above-mentioned medium free of a substance acting on the BMP signal transduction pathway. On day 18 from the start of the floating culture, aggregates are partly recovered, fixed with 4% para-formaldehyde to prepare cryosections. The prepared cryosections are subjected to immunostaining with Chx10 which is one of the neural retinal progenitor markers, based on which the expression of Chx10 in the retinal tissue contained in the cell aggregate produced as mentioned above is examined.

A cell aggregate comprising a ciliary marginal zone-like structure can be produced by the production method of the present invention by using the thus-produced "cell aggregate comprising a retinal progenitor cell" as a "cell aggregate comprising a retinal tissue" to be the starting material.

This application is based on a patent application No. 2013-255836 filed in Japan (filing date: Dec. 11, 2013), the contents of which are incorporated in full herein.

INDUSTRIAL APPLICABILITY

According to the production method of the present invention, a ciliary marginal zone-like structure can be produced with high efficiency.

The invention claimed is:

1. A method for producing a retinal tissue having a ciliary marginal zone-like structure, comprising the steps:
    (a) preparing a cell aggregate from a pluripotent stem cell,
    (b) culturing the cell aggregate to form a retinal tissue comprising 20% or more and 100% or less of cells positive for Chx10,
    (c) culturing the retinal tissue of step (b) in a serum-free medium for a period before the appearance of RPE65-expressing cells, wherein the serum-free medium contains a substance that enhances signal transduction mediated by Wnt and a substance inhibiting the FGF signal pathway, thereby obtaining a retinal tissue having a decreased proportion of Chx10 positive cells that is about 3% or less of the tissue,
    (d) culturing the retinal tissue with the decreased proportion of Chx10 positive cells of step (c) without the substance that enhances signal transduction mediated by Wnt and without the substance inhibiting the FGF signal pathway in a serum-free medium containing a serum replacement or a serum-containing medium to induce the formation of a ciliary marginal zone-like structure in the retinal tissue, and
    (e) obtaining the retinal tissue having the ciliary marginal zone-like structure, wherein the ciliary marginal zone-like structure comprises Rdh10 positive cells.

2. The method according to claim 1, wherein the decreased proportion of Chx10 positive cells in step (c) is within 3% to 0% of the tissue.

3. The method according to claim 1, wherein the culturing in step (d) is until the proportion of Chx10 positive cells present in the retinal tissue reaches 30% or more of the tissue.

4. The method according to claim 1, wherein the pluripotent stem cell is a human pluripotent stem cell.

5. A method of treating a disease due to a disorder of retinal tissue, comprising the steps:
    (a) preparing a cell aggregate from a pluripotent stem cell,
    (b) culturing the cell aggregate to form a retinal tissue comprising 20% or more and 100% or less of cells positive for Chx10,
    (c) culturing the retinal tissue of step (b) in a serum-free medium for a period before the appearance of RPE65-expressing cells, wherein the serum-free medium contains a substance that enhances signal transduction mediated by Wnt and a substance inhibiting the FGF signal pathway, thereby obtaining a retinal tissue having a decreased proportion of Chx10 positive cells that is about 3% or less of the tissue,
    (d) culturing the retinal tissue with the decreased proportion of Chx10 positive cells of step (c) without the substance that enhances signal transduction mediated by Wnt and without the substance inhibiting the FGF signal pathway in a serum-free medium containing a serum replacement or a serum-containing medium to induce the formation of a ciliary marginal zone-like structure in the retinal tissue,
    (e) obtaining the retinal tissue having the ciliary marginal zone-like structure, wherein the ciliary marginal zone-like structure comprises Rdh10 positive cells, and
    (f) transplanting an effective amount of the retinal tissue having the ciliary marginal zone-like structure of step (e) to a subject in need of the transplantation.

6. The method according to claim 1, wherein the culturing of the cell aggregate in step (b) forms a retinal tissue comprising 40% or more of cells positive for Chx10.

7. The method according to claim 1, wherein the culturing of the cell aggregate in step (b) forms a retinal tissue comprising 60% or more of cells positive for Chx10.

8. The method according to claim 1, wherein the culturing of the retinal tissue in step (c) is for 3 to 6 days.

9. The method according to claim 1, wherein the substance that enhances signal transduction mediated by Wnt is a GSK3β inhibitor.

10. The method according to claim 1, wherein the substance that enhances signal transduction mediated by Wnt is CHIR99021.

11. The method according to claim 10, wherein the serum-free medium in step (c) contains about 1 µM to about 30 µM CHIR99021.

12. The method according to claim 1, wherein the substance inhibiting the FGF signal pathway is a FGF receptor inhibitor.

13. The method according to claim 1, wherein the substance inhibiting the FGF signal pathway is SU-5402.

14. The method according to claim 13, wherein the serum-free medium in step (c) contains about 1 µM to about 30 µM SU-5402.

15. The method according to claim 1, wherein, in step (a), the pluripotent stem cell is subjected to floating culture in a serum-free medium to form the cell aggregate, and wherein, in step (b), the cell aggregate is subjected to floating culture in a serum-free medium or serum-containing medium each containing a substance that enhances signal transduction mediated by BMP to form the retinal tissue comprising 20% or more and 100% or less of cells positive for Chx10.

16. The method according to claim 15, wherein the substance that enhances signal transduction mediated by BMP is selected from among BMP2, BMP4, BMP7, and GDF7.

17. The method according to claim 15, wherein the substance that enhances signal transduction mediated by BMP is BMP4.

18. The method according to claim 15, wherein the culturing of the cell aggregate in step (b) forms a retinal tissue comprising 40% or more of cells positive for Chx10.

19. The method according to claim 15, wherein the culturing of the cell aggregate in step (b) forms a retinal tissue comprising 60% or more of cells positive for Chx10.

20. A method for producing a neural retina comprising the steps:
    (a) preparing a cell aggregate from a pluripotent stem cell,
    (b) culturing the cell aggregate to form a retinal tissue comprising 20% or more and 100% or less of cells positive for Chx10, (c) culturing the retinal tissue of step (b) in a serum-free medium for a period before the appearance of RPE65-expressing cells, wherein the serum-free medium contains a substance that enhances signal transduction mediated by Wnt and a substance inhibiting the FGF signal pathway, thereby obtaining a retinal tissue having a decreased proportion of Chx10 positive cells that is about 3% or less of the tissue, (d) culturing the retinal tissue with the decreased proportion of Chx10 positive cells of step (c) without the substance that enhances signal transduction mediated by Wnt and without the substance inhibiting the FGF signal pathway in a serum-free medium containing a serum replacement or a serum-containing medium to induce the formation of a ciliary marginal zone-like structure in the retinal tissue, (e) obtaining the retinal tissue having the ciliary marginal zone-like structure, wherein the ciliary marginal zone-like structure comprises Rdh10 positive cells, and wherein a retinal pigment epithelium and a neural retina are present adjacent to the ciliary marginal zone-like structure, and (f) cutting out the neural retina from the retinal tissue in step (e), thereby obtaining a purified neural retina.

\* \* \* \* \*